United States Patent [19]

Ziegenfuss et al.

[11] Patent Number: 6,086,885
[45] Date of Patent: *Jul. 11, 2000

[54] ANTI-BACTERIAL PROTEIN EXTRACTS FROM SEEDS OF MARIGOLD AND PAPRIKA

[75] Inventors: Steve Ziegenfuss, Des Moines; Friedhelm Brinkhaus, Urbandale; John Greaves, Ankeny, all of Iowa

[73] Assignee: Kemin Industries, Inc., Des Moines, Iowa

[ * ] Notice: This patent issued on a continued prosecution application filed under 37 CFR 1.53(d), and is subject to the twenty year patent term provisions of 35 U.S.C. 154(a)(2).

[21] Appl. No.: 09/057,853

[22] Filed: Apr. 9, 1998

Related U.S. Application Data

[60] Provisional application No. 60/043,225, Apr. 10, 1997.

[51] Int. Cl.$^7$ .......................... A01N 65/00; A61K 35/78
[52] U.S. Cl. .......................... 424/195.1; 514/2; 530/370
[58] Field of Search .......................... 424/195.1; 514/2; 530/370

[56] References Cited

U.S. PATENT DOCUMENTS

| | | | |
|---|---|---|---|
| 4,525,455 | 6/1985 | Zito et al. | 435/135 |
| 5,429,828 | 7/1995 | Fodge et al. | 426/18 |
| 5,514,779 | 5/1996 | Broekaert et al. | 530/379 |
| 5,538,525 | 7/1996 | Broekert et al. | |
| 5,662,915 | 9/1997 | Okioga et al. | 424/408 |

OTHER PUBLICATIONS

Caceres et al. "Plants used in Guatemala for the treatment of gastrointestinal disorders. 1. Screening of 84 plants against enterobacteria". Journal of Ethnopharmacology, 1990, vol. 30, No. 1, pp. 55–73.

Vicente et al. "Effect of administration of dietary paprika seed on *Salmonella enteriditis* on broiler chicks", 1995. Proceeding of the Forty–Fourth Western Poultry Disease conference, Mar. 5–7, 1995. No. 44th, p. 129.

Pellicer et al. "Capsaicin or Feeding with Red Pepers During Gestation Changes the Thermonociceptive Responce of Rat Offspring", Physiology and Behavior, Aug. 1996, vol. 60, No. 2, pp. 435–438.

*Primary Examiner*—Sandra E. Saucier
*Assistant Examiner*—Vera Afremova
*Attorney, Agent, or Firm*—Kent A. Herink, Esq.; Davis Brown Law Firm

[57] ABSTRACT

The present invention describes the method of extraction and the effect of a crude protein extract from the seed tissue of two botanical species, Tagetes and Capsicum, on the survival of two economically important gram-negative bacteria *Salmonella typhimurium* and *Escherichia coli*.

11 Claims, 1 Drawing Sheet

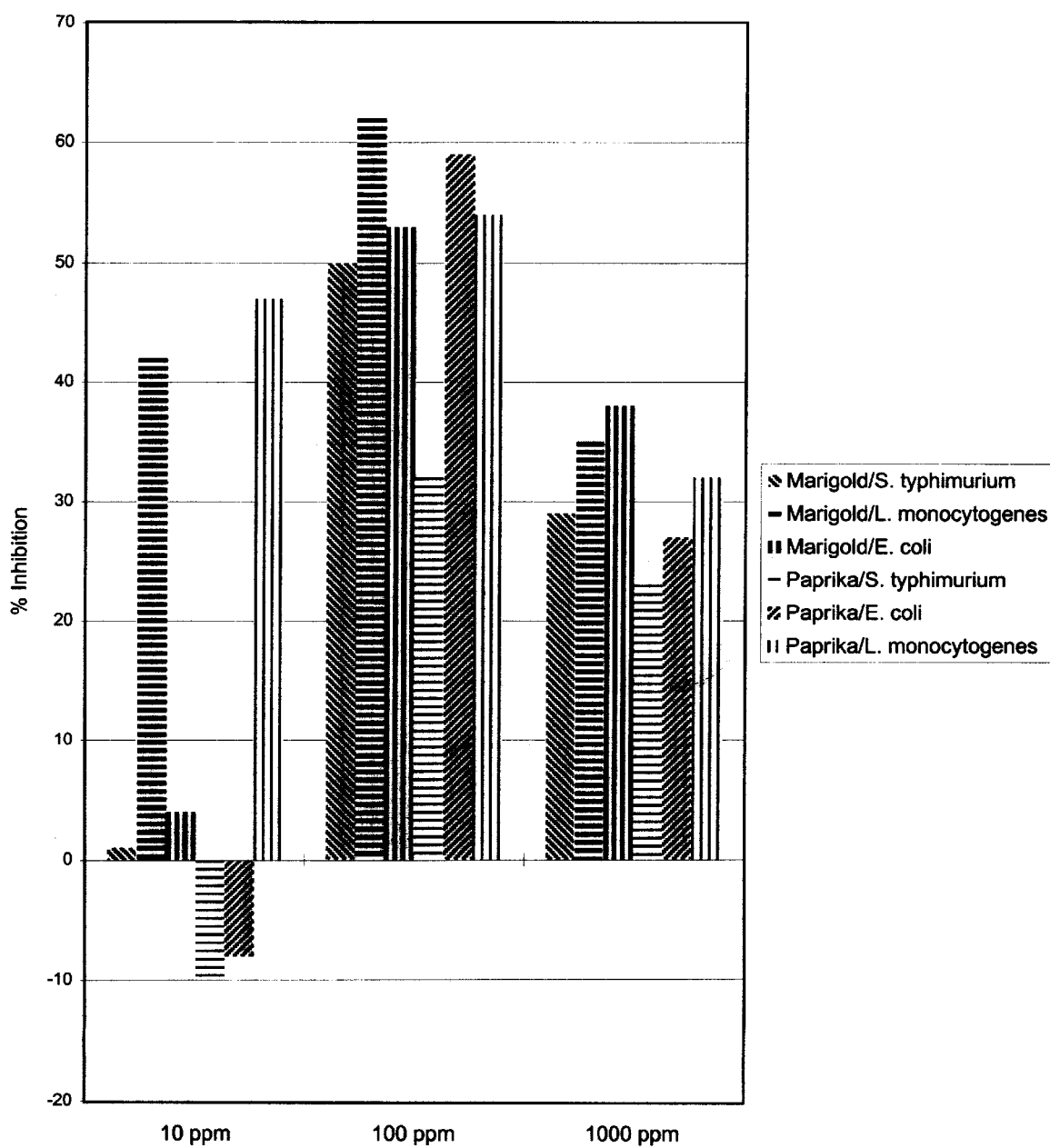

ANTI-BACTERIAL PROTEIN EXTRACTS FROM SEEDS OF MARIGOLD AND PAPRIKA

This application claims the benefit of Provisional Appl. Ser. No. 60/043,225, filed Apr. 10, 1997.

FIELD OF THE INVENTION

The present invention relates to a botanical extract of protein from marigold or paprika that has anti-bacterial activity. More specifically, the present invention relates to proteins having anti-bacterial activity against the gram-negative bacteria Salmonella sp. and *Escherichia coli*. The present invention describes the method of extraction and the effect of a protein extract from the seed tissue of Tagetes sp. or Capsicum sp. on the survival of two economically important bacteria *Salmonella typhimurium* and *E. coli* strain 0157H7. The present invention includes a method for reducing bacteria in animals and animal products, a method of extraction of the genes encoding for the subject proteins, and a method of use of such genes transformed and expressed in grain products such that the resultant grain has anti-bacterial activity.

SUMMARY OF THE INVENTION

The present invention describes the method of extraction and the effect of a crude protein extract from the seed tissue of two botanical species on the survival of two economically important gram-negative bacteria *Salmonella typhimurium* and *Escherichia coli*. Both bacterial organisms are extremely common in animal feed and production animals and are of grave concern in animal agriculture. Transmitted through the food chain, both bacterial organisms cause food poisoning in humans, and control of these organisms is a public health issue of high priority. They also cause economic losses in production animal agriculture through pathogenic effects on the gastrointestinal tracts of monogastric animals, such as poultry and swine. The anti-bacterial proteins are derived from the seeds of marigold (Tagetes sp.) or paprika (Capsicum sp.).

There are several synthetic chemicals such as organic acids and formaldehyde which can be used to control Salmonella and *E. coli* in feeds. However, these chemicals are not without their own concerns on the health of animals and humans. Also, secondary plant products contained in an essential oil fraction have been isolated from many botanical species, among them Tagetes sp., and are known to exhibit strong antimicrobial as well as antifungal activities. Broekaert et al., U.S. Pat. Nos. 5,538,525 and ,514,779 (1996) demonstrated the use of a range of specific peptides derived from botanical species belonging to the Brassicaceae, Compositae and Leguminosae families including Raphanus, Brassica, Sinapis, Arabidopsis, Dahlia, Cnicus, Lathyrus, Clitoria, Amaranthus, Capsicum, Briza and related species on several fungal organisms and on gram-positive bacteria. However, they did not describe any effect on gram-negative bacteria. To our knowledge there are no documented examples of natural, plant-derived proteins or peptides which have a significant biocidal effect on gram-negative bacteria such that they could be used to control these organisms in a range of applications. In addition, there are no reports on antimicrobial or antifungal proteins characterized in Tagetes. The present invention describes novel proteins from two botanical sources and their effect on more important gram-negative bacteria.

The proteins extracted from the seeds of such botanical species can be used to control Salmonella and *E. coli* in animal feeds and human foods. Furthermore, the proteins and the genes that code for them could be sequenced and manipulated via genetic engineering techniques for expression in production microorganisms via fermentation. In addition, the genes could be expressed in the seeds of economically important crops such as corn, soybean, wheat and rice for inclusion of such anti-bacterial proteins in the downstream processing and use of these grains in animal feed and human food. Production of proteins via genetic engineering of microbes and plants followed by fermentation or agronomic production is now common place and established practice. Overproduction of secondary plant products via pathway engineering, on the other hand, is still technically a challenge.

BRIEF DESCRIPTION OF THE DRAWINGS

FIG. 1 is a graphical representation of anti-bacterial inhibition data of the proteins of the present invention.

DETAILED DESCRIPTION OF THE INVENTION

The present invention relates to a crude protein extract, the purified protein(s), and the gene(s) encoding for the protein that are extracted from marigold and paprika. The protein inhibits the activity of *E. coli* (strain 0157H7) and possibly also *S. enteritidis* and *S. choleraesuis*. The protein also inhibits *Salmonella typhimurium* and *Listeria monocytogenes*.

The present invention is protein(s), and the gene encoding such proteins, which inhibit the growth of the gram-negative bacteria. These proteins are naturally-occurring in the seeds of marigold. These proteins can be used in the raw form, as a crude protein extract, and applied to animal feed or human foodstuff (particularly those foodstuff that are high in *E. coli* or *Salmonella typhimurium*.). The proteins can be purified and applied to feed for animals and foodstuff for humans. Alternatively, the proteins can be applied directly to places in which bacteria multiply.

The genes encoding for these proteins can be transformed into bacteria, fungi, yeasts, plants, or mammals (prokaryotic or eukaryotic cells), and the protein can be harvested and applied directly to the bacteria. Additionally, the proteins can be produced within the cells of the material that carries the bacteria. For example, the proteins can be produced in the grains of material in animal foods. In chicken feed, the proteins can be expressed in the petals or seeds of the marigold flower and supplied as marigold meal (that is supplied for its lutein) which can be added as a feed additive. A number of cereal grains could be transformed so that the protein was expressed in the seed. The transgenic corn, soybean, canola, peanut, oat, wheat, barley, rice, sugarbeet, cotton, or tobacco seed can have the protein expressed therein. Thus, when the grain is prepared for animal feed or for human food products, the protein is released from the seed and is active in decreasing the bacteria present in the grain or feed product, in the animal that is fed the feed product, and in the meat of animals fed the feed product. The proteins can also be placed in soaps, face, and hand cleansers, as an antimicrobial, and in surface cleansers to decrease bacterial contamination.

Transgenic corn, soybean, canola, peanut, oat, wheat, barley, rice, and other transformable fruits, vegetables, and plants can have the protein expressed in tissue other then the seed. Thus, when the fruit, vegetable, or other plant tissue or forage is prepared for feeding, the bacteria are decreased. This is particularly useful for the preparation of silage from corn and sorghum.

Additionally, the present invention has usefulness in the pharmaceutical field and the fields of veterinary science. Clearly, if the bacteria are present in the digestive system, the mammal can ingest the protein to decrease the bacteria present. Because many bacteria are in the gut, by encapsulating the protein material or forming the protein in material that is not broken down until it reaches the gut, the protein material can be useful as a method of decreasing the bacteria in the human or animal digestive system. Alternatively, the protein could be injected directly into the mammals' intestines or other digestive organs.

The crude protein extract of the present invention is run on a protein gel to separate the proteins in the extract. The proteins are then purified, and each protein is tested against the listed gram-negative bacteria for the inhibition effects. The protein, and/or proteins with the most inhibiting effects, is sequenced by known sequencing methods. The methods to do this type of screening experiment and the procedures involving gene sequencing and vector production are clearly outlined in *Current Protocols in Molecular Biology*, published by John Wiley and Sons, New York (1995). This manual, or the short protocols of this manual, can be. found in most biotechnology labs.

Transformation Methods—are means for integrating new genetic coding sequences into the target organism's genome by the incorporation of these sequences into an organism through man's assistance.

Using the sequence of the protein, the DNA encoding for such protein could be isolated and used, via known procedures, to transform a suitable host organism such that the protein is produced by the recombinant host in commercially useful amounts. The protein encoding DNA could be reverse-engineered using codons that are acceptable and recognizable to the host. Alternatively, the gene could be isolated by screening nucleic acid libraries of species which produce the protein. Oligonucleotide probes that are complementary to a polynucleotide encoding a portion of the protein, for example, a N-terminus sequence, can be employed to locate the gene. Probes can be employed in a known manner to screen a genomic or cDNA encoding library or to synthesis polymerase chain reaction (PCR) probes for the amplification of the cDNA encoding for isolates from an RNA which translated into the protein of the present invention. Such cDNA could then be cloned into a suitable expression vector for the selected host and transformed into a host organism. One of the typical host organisms is *E. coli*. This is not a particularly useful host for the purposes of this invention because the protein inhibits the host. Thus, the host would have to be selected to be capable of producing the protein without the protein harming the host.

The vector for transformation would preferably comprise a nucleotide sequence that corresponds to the protein amino acid sequence that may be optimized for the selected host. The vector would also be designed with regard to codon selection, the initiation of translation, the promoter, and the targeting sequences, if needed, to maximize the expression of recoverable amounts of the protein. Vectors for hosts such as plants, algae, insects, animals, yeasts, fungi, bacteria, and humans are commercially available from companies such as Novagon, and a number of other sources. Vectors for different hosts are described in the in *Current Protocols In Molecular Biology*.

There are a large number of known methods to transform plants. However, certain types of plants are more amenable to transformation than are others. Tobacco is a readily transformable plant, and its transformation is well-published. Most dicots can be transformed by the methods used to transform tobacco. Monocots are transformed by different methods which are also widely-published, and, thus, the basic steps of transforming plants, including monocots, are known in the art.

These steps are concisely outlined in U.S. Pat. No. 5,484,956 "Fertile Transgenic *Zea mays* Plants Comprising Heterologous DNA Encoding Bacillus Thuringiensis Endotoxin", issued Jan. 16, 1996, and in U.S. Pat. No. 5,489,520 "Process of Producing Fertile *Zea mays* Plants and Progeny Comprising a Gene Encoding Phosphinothricin Acetyl Transferase", issued Feb. 6, 1996.

Plant cells, such as maize, can be transformed by a number of different techniques. Some of these techniques, which have been reported on and are known in the art, include maize pollen transformation (see, U.S. Pat. No. 5,177,010, University of Toledo (1993)); biolistic gun technology (see, U.S. Pat. No. 5,484,956); whiskers technology (see, U.S. Pat. Nos. 5,464,765 and 5,302,523); electroporation (see, PEG on Maize); Agrobacterium (see, 1996 article on transformation of maize cells in *Nature Biotechnology*, Volume 14, June 1996); and numerous other methods which may have slightly lower efficiency rates than those listed.

Some of these methods require specific types of cells, and other methods can be practiced on any number of cell types. The use of pollen, cotyledons, meristems, and ovum as the target tissue can eliminate the need for extensive tissue culture work. However, the present state of the technology does not provide very efficient use of some of this material.

Generally, cells derived from meristematic tissue are useful for transformation as they are very regenerable. Zygotic embryos can also be used. The method of transformation of meristematic cells of cereal is taught in the PCT application WO96/04392. Any of the various cell lines, tissues, plants, and plant parts can be, and have been, transformed by those having knowledge in the art. Methods of preparing callus from various plants are well-known in the art, and specific methods are detailed in patents and references used by those skilled in the art.

Cultures can be initiated from most of the above-identified tissue. The only true requirement of the transforming material is that it can form a transformed plant.

The DNA used for transformation of these plants clearly may be circular, linear, double, or single stranded. Usually, the DNA is in the form of a plasmid. The plasmid usually contains regulatory and/or targeting sequences which assist the expression of the gene in the plant. The methods of forming plasmids for transformation are known in the art. Plasmid components can include such items as leader sequences, transit polypeptides, promoters, terminators, genes, multiple gene copies, introns, and marker genes. The structures of the gene orientations can be sense, antisense, partial antisense, or partial sense.

The regulatory promoters employed can be constitutive, such as CaMv35S (usually for dicots) and polyubiquitin for monocots, or tissue specific promoters such as CAB promoters. The prior art includes, but is not limited to, octopine synthase, nopaline synthase, CaMv19S, and mannopine synthase promoters. These regulatory sequences can be combined with introns, terminators, enhancers, leader sequences, and the like, in the material used for transformation.

The isolated DNA is then transformed into the plant. The improvements in transformation technology are beginning to eliminate the need to regenerate plants from cells. Since 1986, the transformation of pollen has been published, and recently, the transformation of plant meristems have been published. The transformation of ovum, pollen, and seedlings meristem greatly reduce the difficulties associated with cell regeneration of different plants or genotypes within a plant. Duncan, from at least 1985–1988, produced literature on plant regeneration from callus. Somatic embryogenesis has been performed on various maize tissue which was once considered unusable for this purpose. The prior art clearly teaches the regeneration of plants from various monocot and dicot tissues.

The most common method of transformation is referred to as gunning or microprojectile bombardment. This biolistic process shoots small, gold-coated particles coated with DNA into the transformable material. Techniques for gunning DNA into cells, tissue, callus, embryos, and the like, are well-known in the prior art.

After the transformation of the plant material is complete, the next step is identifying the cells or material which has been transformed. In some cases, a screenable marker is employed, such as the beta-glucuronidase gene of the uida locus of $E.\ coli$. Then, the transformed cells expressing the colored protein are selected for either regeneration or further use. In many cases, the transformed material is identified by a selectable marker. The putatively transformed material is exposed to a toxic agent at varying concentrations. The cells which are not transformed with the selectable marker that provides resistance to this toxic agent die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cellular, then these cells are regenerated into plants. The plants created from either the transformation process or the regeneration process, or crossed to either of such plants or a progeny of such plants, are transgenic plants.

The protein of the present invention was extracted from the plant seeds via the following process:

EXAMPLE 1

Preparation of Protein Extract from Marigold and Paprika Seeds

Aqueous extraction was followed by ammonium sulfate precipitation in the interval of 30% to 70% relative saturation, heat precipitation at 80° C., and dialysis for 3 days. The detailed methods are described below.

Five hundred grams of marigold seeds (*Tagetes erecta*) or 250 g of paprika seeds (Capsicum sp.) were ground in a coffee mill and extracted for 2 hours in 2.0 liters (marigold) or 1.0 liters (paprika) of extraction buffer at 4° C. The extraction buffer contained 10.0 mM $NaH_2PO_4$, 15.0 mM $Na_2HPO_4$, 100.0 mM KCl, 2.0 mM EDTA (ethylenediaminetetraacetic acid) disodium salt, 2.0 mM thiourea and 1.0 mM PMSF (phenylmethylsulfonyl fluoride) (dissolved in MeOH). The homogenate was squeezed through cheesecloth and centrifuged for 30 min. at 7000× g. The pellet was discarded, and the supernatant was retained. The supernatant was brought to 30% relative saturation with ammonium sulfate and precipitated overnight. The precipitate was removed by centrifugation at 7000× g for 30 minutes. The supernatant was adjusted to 70% relative saturation with ammonium sulfate and precipitated overnight. The precipitate was collected by centrifugation at 7000× g for 30 min. The pellet was re-suspended in 400.0 ml R.O. (reverse osmosis) water and heat precipitated in a water bath for 30 minutes at 80° C. The precipitate was collected by centrifugation at 7000× g, and the supernatant was dialyzed against R.O. water for 3 days using cellulose ester dialysis tubing with a molecular weight cut-off of 1000 daltons (SpectralPor, Spectrum, USA). The water was changed 3 times on day 1, and once each day for days 2 and 3. The dialyzed supernatant was then frozen to −60° C. and freeze-dried.

EXAMPLE 2

Antibacterial Activity Assay

This method was repeated for the marigold and paprika extracts. A spectrophotometrical method was used where the optical density of bacterial cultures was determined when grown in micro-titer plates.

For appropriate dilution of the protein extracts from marigold and paprika, 0.1 gram of the protein extract was blended with 10.0 grams dextrose to achieve a homogenous, free-flowing mixture. One gram of the protein extract/dextrose preparation was then dissolved in 2.0 ml of saline solution and serially diluted in sterile saline. Twenty microliters of the appropriately diluted solution were then added to the inoculated wells of the micro-titer plate to achieve 10 ppm, 100 ppm, or 1000 ppm treatment rates. Next, 80 µl of a 24 hour trypticase soy broth (TSB) culture of *Salmonella typhimurium, E. coli,* or *Listeria monocytogenes* was added to the wells of a micro-titer plate. Twelve wells per organism per treatment rate were used and 12 further wells were used as a control series. For the controls, sterile saline, instead of the diluted protein extract, was added to the wells.

The micro-titer plates were then incubated 18 hours at 37° C., and the optical density of the wells were subsequently determined spectrophotometrically at 405/410 nm. As a blank, sterile TSB was used.

EXAMPLE 3

Antibacterial Activity of the Protein Extracts from Marigold and Paprika

The antibacterial potency of the protein extracts from marigold and paprika were evaluated against three gram-negative bacteria, *Salmonella typhimurium, E. coli,* and *Listeria monocytogenes*. Potency was measured as described in Example 2. The three bacteria were tested at 3 different treatment levels, 10 ppm, 100 ppm and 1000 ppm, and each treatment level was replicated 12 times. After 18 hours incubation, growth of bacteria was measured as optical density as described above. The results, in percentage of the optical density of the control as mean values for the 12 replicates, are presented in Table 1. The student's t-test was conducted to test for statistical significance with P<0.01 indicating statistical significance.

TABLE 1

Inhibition of *S. typhimurum*, *E. coli* and *L. monocytogenes* by protein extracts from marigold and paprika as % of control

| Bacterium/Treatment | Marigold (% of ctrl) | T-Test | Paprika (% of ctrl) | T-Test |
|---|---|---|---|---|
| *Salmonella typhimurium* | | | | |
| 10 ppm | 99.0 | 0.74 | 110.0 | <0.01 |
| 100 ppm | 50.0 | <0.01 | 68.0 | <0.01 |
| 1000 ppm | 71.0 | <0.01 | 77.0 | <0.01 |
| *E. coli* | | | | |
| 10 ppm | 96.0 | 0.06 | 108.0 | 0.14 |
| 100 ppm | 47.0 | <0.01 | 41.0 | <0.01 |
| 1 000 ppm | 62.0 | <0.01 | 73.0 | <0.01 |
| *Listeria monocytogenes* | | | | |
| 10 ppm | 58.0 | <0.01 | 53.0 | <0.01 |
| 100 ppm | 38.0 | <0.01 | 46.0 | <0.01 |
| 1 000 ppm | 65.0 | <0.01 | 68.0 | <0.01 |

The results of the gram-negative bacteria study clearly show that there is over a 50% bacterial inhibition at the 100 ppm level. The data of TABLE 1 is illustrated graphically in FIG. 1.

EXAMPLE 4

Isolation and Purification of Heat Stable Protein Fraction (HSPF)

Upon isolation of the heat stable protein fraction (HSPF), microbial inhibitory assays were performed to assay the growth of gram-negative bacteria. These tests verified the inhibiting effects of the HSPF. Once the efficacy was established, the functional protein, or proteins, of interest were isolated from the HSPF fraction. About 100 mg of the heat-stable protein fraction dissolved in 50 mm MES (pH 6.0) was applied on a Toyopearl Sp-550C cation exchange column (10×1.6 cm), previously equilibrated with MES buffer. The column was eluted at 5.0 ml/min using a step gradient elution ranging from 100 mM to 1 M NaCl. Each fraction eluted from the column was analyzed at 280 nm for any protein activity. Those fractions that showed significant presence were then dialyzed into neutral DI water. Upon completion of dialysis, the fractions of interest were concentrated with 60% w/v polyethylene glycol (PEG) and then lyophilized. The dry protein extracts were then tested using the same assay that was used for the HSPF. Any fractions showing positive inhibition were then analyzed by electrophoresis using the Pharmacia phastgel system on a 8-25 gradient gel. Upon establishing the inhibiting effects of the fractions and the protein content of each respective fraction through electrophoresis, the fraction(s) were passed over a Sephacryl S-100 HR in phosphate buffer (0.05 M, pH 7.00) to remove any residual or undesired protein isolates. The fractions were then reanalyzed on the phastgel system using a homologous gel to provide greater resolution of the purified protein(s) of interest. The fractions showing antibacterial activity were further analyzed by reversed phase chromatography. About 1 mg amounts of peak 1 material from the Sephacryl column purification run were loaded onto a silica C18 column (25×93 cm) in equilibrium with 0.1% TFA. The column was eluted at 5 ml/min with a linear gradient of 150 ml from 0.1% trifluoroacetic acid (TFA) to 50% acetonitrile/0.2% TFA. The elute was monitored for protein by online measurement of absorption at 214 nm. Once satisfactory purification was achieved, and its presence accounted for the inhibitory effects of microbial growth, the protein was ready for sequencing.

EXAMPLE 4

Isolation of Gram-Negative Inhibiting Protein from Marigolds and Paprika

Marigolds and paprika produce the desired proteins in the seed of the plant. The present experiment is adapted to increase the production of that protein. The inhibition of the gram-negative bacteria by the protein can be improved by the introduction of the gene that encodes for the desired protein into marigold or paprika. Additionally, the protein can be accumulated in larger seeds such as the tobacco seed. A plasmid, adapted from a plasmid such as pATCC1616, ATCC accession No. 40806, can have the phytoene dehydrogenase-4H encoding gene removed and the selected gene inserted by known restriction site technology. Alternatively, other starting plasmid material can be purchased for this purpose. The plasmid is characterized by the ability to be maintained in *Agrobacteruim tumefaciens*, which is used to infect the tobacco or a number of other dicots. The plasmid also has the right and left borders of the sequence of the T-DNA and a promoter associated with the kanamycin resistance gene in the presence of that antibiotic. The plasmid is transformed into *Agrobacterium tumefaciens* strain LBA4404 (CLONTECH, Inc.) according to standard protocols. The tobacco leaf disc are transformed with Agrobacteruim using the method of Horsch et.al., Science, 227:1229–1231 (1985). The selectable marker gene gives resistance to the herbicide norflurazon (Sandoz; 0.8 micrograms per milliliter). The plant cells that are transformed do not die in the present of the herbicide. The transgenic plants are grown from the transformed cells, and the seeds are harvested. Then, five hundred grams of the tobacco seed are ground in a coffee mill and extracted according to the procedure above for 2 hours in 2 liters of extraction buffer at 4° C. The plasmid used for transformation can be improved by the use of a promoter that targets the seed. Examples of seed promoters are known in the art, such as the maize zein storage promoter. Alternatively, the protein can be produced constitutively throughout the plant with the use of the 35S CAMV promoter, for example. Examples of genetically modified plants which may be used to produce grain or other plant parts which express the protein include maize, soybean, sunflower, wheat, barley, sorghum, canola, peanut, oats, sugar beet, rice, and tobacco.

A similar transformation of fungi or bacteria can be performed. The starting plasmid would include a promoter recognized by the host and the selectable marker is often an antibiotic. The protein product is lysed from the cell. To produce large quantities a fermentation process for producing the protein can be used.

Although the invention has been described with respect to a preferred embodiment thereof, it is to be also understood that it is not to be so limited since changes and modifications can be made therein which are within the full intended scope of this invention as defined by the appended claims.

We claim:

1. A proteinaceous extract which has antibacterial activity against gram-negative bacteria made by the process of:
   extracting seeds from Tagetes sp. or Capsicum sp with an aqueous solution to form a first supernate and insolubles,
   separating the first supernate from the insolubles;
   adding ammonium sulfate to 30% relative saturation as a precipitating agent thereby precipitating a first fraction and forming a second supernate;
   collecting the second supernate;
   adding amonium sulfate to 70% relative saturation as a precipitating agent thereby precipitating a second fraction and forming a third supernate;
   dissolving the second precipitate fraction in an aqueous medium;
   heating the aqueous medium, which contains the second precipitate fraction, to 80° C. thus forming a third precipitate and a third supernate;
   separating the third supernate;
   dialyzing the third supernate using a 1000 Dalton molecular weight cut off membrane; and
   collecting the dialyzed supernate which does not pass through the membrane.

2. The proteinaceous extract of claim 1 wherein the gram-negative bacteria are selected from the group consisting of *Escherichia coli,* Listeria and Salmonella.

3. The proteinaceous extract of claim 1, wherein the gram-negative bacteria is strain 0157:H7 of *Escherichia coli.*

4. The proteinaceous extract of claim 1, wherein the seeds are from Tagetes sp. and the gram-negative bacteria is *Salmonella typhimurium.*

5. The proteinaccous extract of claim 1, wherein the gram-negative bacteria is *Listeria monocytogenes.*

6. The proteinaccous extract of claim 1, wherein the Tagetes sp. is *Tagetes erecta.*

7. The proteinaceous extract of claim 1, wherein the Capsicum sp is *Capsicum annum.*

8. An animal feed composition having anti-bacterial activity comprising a feed to which the proteinaccous extract of claim 1 is added in an amount effective to reduce populations of gram-negative bacteria in an animal.

9. A method of reducing a population of gram negative bacteria in an animal comprising adding the proteinaceous extract of claim 1 to a feed and orally administering the feed to the animal in an amount effective to reduce the population of gram-negative bacteria in the animal.

10. The method of claim 9, wherein the proteinaceous extract, after freeze drying, is added in an amount of between 0.01 ppm and 1000 ppm by weight of the untreated feed.

11. A method of reducing the bacterial load of meat comprising adding the proteinaceous extract of claim 1 to a feed and orally administering the feed to an animal to be used for meat in an amount effective to reduce the population of gram-negative bacteria in the animal.

* * * * *